(12) United States Patent
Ammann

(10) Patent No.: US 6,825,382 B2
(45) Date of Patent: Nov. 30, 2004

(54) TRIFLUOROMETHYLEPINEPHRINE COMPOUNDS AND METHODS OF MAKING AND USING THEREOF

(75) Inventor: Jeffrey R. Ammann, Round Lake, IL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/376,311

(22) Filed: Mar. 3, 2003

(65) Prior Publication Data

US 2004/0015015 A1 Jan. 22, 2004

Related U.S. Application Data

(60) Provisional application No. 60/361,510, filed on Mar. 4, 2002.

(51) Int. Cl.[7] ................. C07C 215/78; C07C 217/84; C07C 217/86; C07F 7/04; C07F 7/10
(52) U.S. Cl. .................. 564/365; 556/417; 514/653
(58) Field of Search ................. 564/365; 556/417; 514/653

(56) References Cited

PUBLICATIONS

Adejare, A., et al. (1988) "Syntheses and Andrenergic Activities of Ring–Fluorinated Epinephrines" J. Med. Chem. 31:1972–1977.
Allgire, J.F., et al. (1985) "High–Performance Liquid Chromatographic Determination of d–ll –Epinephrine Enantiomer Ratio in Lidocaine–Epinephrine Local Anesthetics" J. of Chromatography 325:249–254.
Amino Amide Local Anesthetics, Cleveland Clinic Foundation, Dept. of Gen. Anesthesiology, (2002) http://old.weber.edu/ewalker/Medicinal_Chemistry/topics/Psycho/local_a_amide.htm, pp 1–3.
Anesthetics, Types, (2002) http://cortex.uchc.edu/emres/anesthetics.htm, pp 1–3.
Britz–Mckibbin, P., et al. (1999) "Analysis of Epinephrine From Fifteen Different Dental Anesthetic Formulations by Capillary Electrophoresis", J. of Chromatography A 853:535–540.
Britz–McKibbin, P., et al. (1998) "Quantitative Assay for Epinephrine in Dental Anesthetic Solutions by Capillary Electrophoresis" 123:1461–1463.
Chen, G.T., et al., ((1993) "Syntheses of 2,5–and 2,6–Difluorepinephrine, 2,5–Difluoroepinephrine, and 2,6–Difluorophenylephrine: Effect of Disubstitution with Fluorine on Adrenergic Activity" J. Med. Chem. 36:3947–3955.
Fanali, S., et al. (1990) "Enantiomer Resolution by Using Capillary Zone Electrophoresis: Resolution of Racemic Tryptophan and Determination of the Enantiomer Composition of Commercial Pharmaceutical Epinephrine" Electrophoresis 11:757–760.

Hondrum, S.O., et al., (1993) "Stability of Local Anesthetics in the Dental Cartridge" Anesthesia & Pain Control in Dentistry, 2(4):198–202.
Kirk, K.L., et al., (1979) "Synthesis and Biological Properties of 2–, 5–, and 6–Fluoronorepinephrines" J. Medicinal Chem. 22(12):1493–1497.
Local Anesthesia and Regional Anesthetics (2002) http://www.anesthesia.wisc.edu/med3/localanes/localhandout.html, pp 1–8.
Lu, S., et al., (2000) "Syntheses of (R)–and (S)–2–and 6–Fluoronorepinephrine and (R)–and (S)–2–and 6–Fluoroepinephrine: Effect of Stereochemistry on Fluorine–Induced Adrenergic Selectivities" J. Med. Chem. 43:1611–1619.
Markovich, K.M., et al., (1992) "Synthesis of Halogenated Trimetoquinol Derivatives and Evaluation of Their β–Agonist and Thromboxane $A_2$ ($TXA_2$) Antagonist Activities" J. Med. Chem. 35:466–479.
Matsui, K., et al., (1981) "A Convenient Trifluoromethylation of Aromatics Halides With Sodium Trifluoroacetate" Chemistry Letters pp. 1719–1720.
Milano, E.A., et al., (1982) "Aluminum Catalysis of Epinephrine Degradation in Lidocaine Hydrochloride Epinephrine Solutions" J. of Parenteral Science and Tech. 36(6):232–236.
Milano, E.A., et al., (1983) "The Formation of an Aluminum–Epinephrine Complex and Its Effect on the Addition of Bisulfite to Epinephrine" J. Parenteral Science and Technology 37(5):165–169.

(List continued on next page.)

*Primary Examiner*—Brian Davis
(74) *Attorney, Agent, or Firm*—Elizabeth Arwine

(57) ABSTRACT

Disclosed herein are trifluoromethylepinephrine compounds having the following structural formula (I)

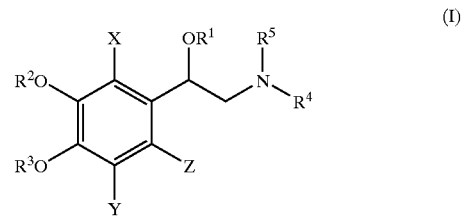

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio; wherein X, Y, and Z are each independently selected from the group consisting of H or trifluoromethyl with the proviso that at least one of which is trifluoromethyl. Also disclosed are pharmaceutical compositions comprising the trifluoromethylepinephrine compounds and methods of making and using thereof. Novel trifluoroepinephrine intermediates are also disclosed.

22 Claims, 3 Drawing Sheets

OTHER PUBLICATIONS

Peterson, T.E., et al., (1992) "Quantitation of l–epinephrine and Determination of the d–ll–epinephrine Enantiomer Ratio in a Pharmaceutical Formulation by Capillary Electrophoresis" J. of Chromatography, 603:298–301.

Welsh, L. (1955) "The Analysis of Solutions of Epinephrine and Norepinephrine" J. Amer. Pharm. Assoc. XLIV, 8:507–514.

Zhong–Yuan, Y., et al. (1989) "Investigation on the Enantiomeric Impurity of Epinephrine Hydrochloride Injections" Chirality 1:92–93.

TRIFLUOROMETHYLEPINEPHRINE COMPOUNDS AND METHODS OF MAKING AND USING THEREOF

CROSS REFERENCE TO RELATED APPLICATIONS

This application is related to U.S. Provisional Patent Application No. 60/361,510, filed Mar. 4, 2002, abandoned, naming Jeffrey R. Ammann as the inventor, which is herein incorporated by reference in its entirety.

ACKNOWLEDGMENT OF GOVERNMENT SUPPORT

This invention was jointly made by employees of the United States Army. The government has certain rights in the invention.

BACKGROUND OF THE INVENTION

1. Field of the Invention

This invention relates generally to trifluoromethylepinephrine compounds and methods of making and using thereof.

2. Description of the Related Art

Anesthetic failures are common in general dental practices. See Kaufman, E. et al. (1984) J. Am. Dent. Assoc. 108–205–208. The causes of anesthetic failure relate to provider/patient factors such as technique, location of injection, anatomy, patient variability and pharmaceutical factors such as concentration and potency, pKa and pH, absorption, distribution, metabolism, excretion, degradation, and storage stability. See Hondrum, S., et al. (1993) Anesthesia & Pain Control in Dentistry 2(4):198–202.

Degradation of a pharmaceutical may occur by chemical, physical, or biological processes. The primary chemical processes that cause degradation are hydrolysis, oxidation, racemization, radiation, and incompatibility. Although degradation by hydrolysis is common with ester based local anesthetics, amide-based local anesthetics such as lidocaine and mepivacaine and the like are resistant to hydrolysis. See Cartwright, P. D. and Fyhr, P. (1988) Regional Anesth. 13:1–12. See Linter, C. J. (1980); and REMINGTON: THE SCIENCE AND PRACTICE OF PHARMACY 20$^{th}$ ed. Lippincott Williams & Wilkins Baltimore, Md. (2000). As amide-based anesthetics are resistant to degradation, the shelf life of dental preparations is dependent on the stability of the vasoconstrictor used.

Epinephrine and epinephrine derivatives are vasoconstrictors that are used to prolong the activity of local anesthetics in dental preparations. Epinephrine is degraded by racemization, oxidation, and bisulfite addition. See Milano, E. A., et al. (1982) J. Parenter. Sci. Technol. 36(6):232–236. It is reported that epinephrine in dental preparations may decrease to less than 85 to 90% of the initial concentration when stored under optimal conditions and less than 70% when stored under clinical conditions. See e.g. Cassidy, J. P. et al. (1986) Anesth. Prog. 33:289–297; and Gerke, D. C. et al. (1977) Aust. Dent. J. 22(6):423–427.

In some instances, it is not possible to store local anesthetics under optimal or even clinical conditions. For example, in military settings, local anesthetics are stored under harsh environmental conditions, e.g. above ambient temperatures. Therefore, there is a need for vasoconstrictors, local anesthetics, and dental preparations that exhibit enhanced resistance to hydrolysis and oxidation and a longer shelf life.

SUMMARY OF THE INVENTION

The present invention generally relates to trifluoromethylepinephrine compounds and methods of making and using the trifluoromethylepinephrine compounds.

In some embodiments, the present invention provides a compound having the following structural formula (I):

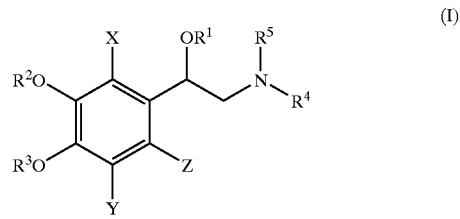

(I)

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio; wherein X, Y, and Z are each independently selected from the group consisting of H or trifluoromethyl with the proviso that at least one of which is trifluoromethyl.

In some preferred embodiments, $R^1$–$R^5$ are each independently selected from the group consisting of H and methyl. In some embodiments, X is trifluoromethyl, Y is trifluoromethyl, or Z is trifluoromethyl. In some embodiments, $R^1$–$R^4$ are methyl and $R^5$ is H.

In preferred embodiments, the compound is 2-trifluoromethylepinephrine, 5-trifluoromethylepinephrine, or 6-trifluoromethylepinephrine.

In some embodiments, the compound is an (S)-enantiomer. In other embodiments, the compound is an (R)-enantiomer.

In some embodiments, the present invention provides a pharmaceutical composition comprising a pharmaceutically acceptable carrier and a compound having the following structural formula (I):

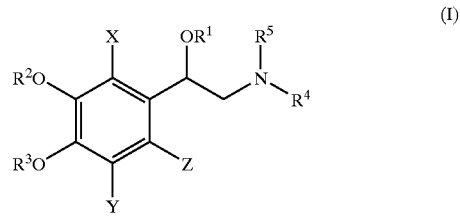

(I)

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio; wherein X, Y, and Z are each independently selected from the group consisting of H or trifluoromethyl with the proviso that at least one of which is trifluoromethyl.

In some preferred embodiments, $R^1$–$R^5$ are each independently selected from the group consisting of H and methyl. In some embodiments, X is trifluoromethyl, Y is trifluoromethyl, or Z is trifluoromethyl. In some embodiments, $R^1$–$R^4$ are methyl and $R^5$ is H.

In preferred embodiments, the compound is 2-trifluoromethylepinephrine, 5-trifluoromethylepinephrine, or 6-trifluoromethylepinephrine.

In some embodiments, the compound is an (S)-enantiomer. In other embodiments, the compound is an (R)-enantiomer.

In some embodiments, the pharmaceutical composition further comprises a supplementary active compound. In preferred embodiments, the supplementary active compound is an analgesic. In more preferred embodiments, the analgesic is a local analgesic.

The present invention also provides a compound having the following structural formula (9)

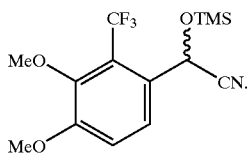

(9)

The present invention also provides a compound having the following structural formula (10)

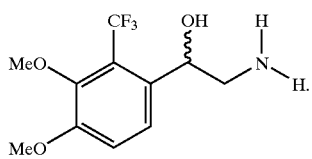

(10)

The present invention also provides a compound having the following structural formula (11)

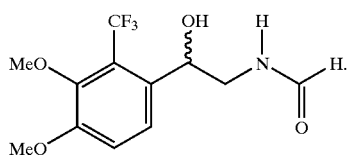

(11)

The present invention also provides a compound having the following structural formula (12)

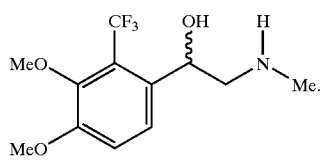

(12)

The present invention also provides a method of making 2-trifluoromethylepinephrine which comprises using 3,4-dihydroxy-2-trifluoromethyl-benzaldehyde or 3-hydroxy-4-methoxybenzaldehyde as a starting product.

The present invention provides a method of detecting, measuring, or analyzing at least one epinephrine derivative in a sample which comprises conducting HPLC analysis and chiral separation on the sample.

The present invention also provides a method of inducing localized vasoconstriction in a subject which comprises administering to the subject a compound having the following structural formula (I):

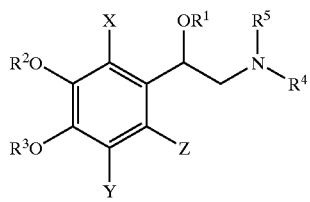

(I)

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio; wherein X, Y, and Z are each independently selected from the group consisting of H or trifluoromethyl with the proviso that at least one of which is trifluoromethyl. In some preferred embodiments, the compound is 2-trifluoromethylepinephrine, 5-trifluoromethylepinephrine, or 6-trifluoromethylepinephrine.

In some embodiments, the present invention also provides a method of treating a disease or a disorder associated with vasodialation in a subject which comprises administering to the subject a compound having the following structural formula (I):

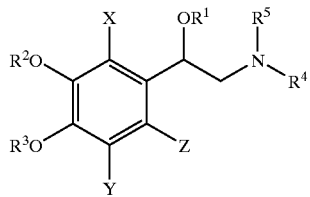

(I)

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio; wherein X, Y, and Z are each independently selected from the group consisting of H or trifluoromethyl with the proviso that at least one of which is trifluoromethyl. In some preferred embodiments, the compound is 2-trifluoromethylepinephrine, 5-trifluoromethylepinephrine, or 6-trifluoromethylepinephrine.

DESCRIPTION OF THE DRAWINGS

This invention is further understood by reference to the drawings wherein.

Figure 1:
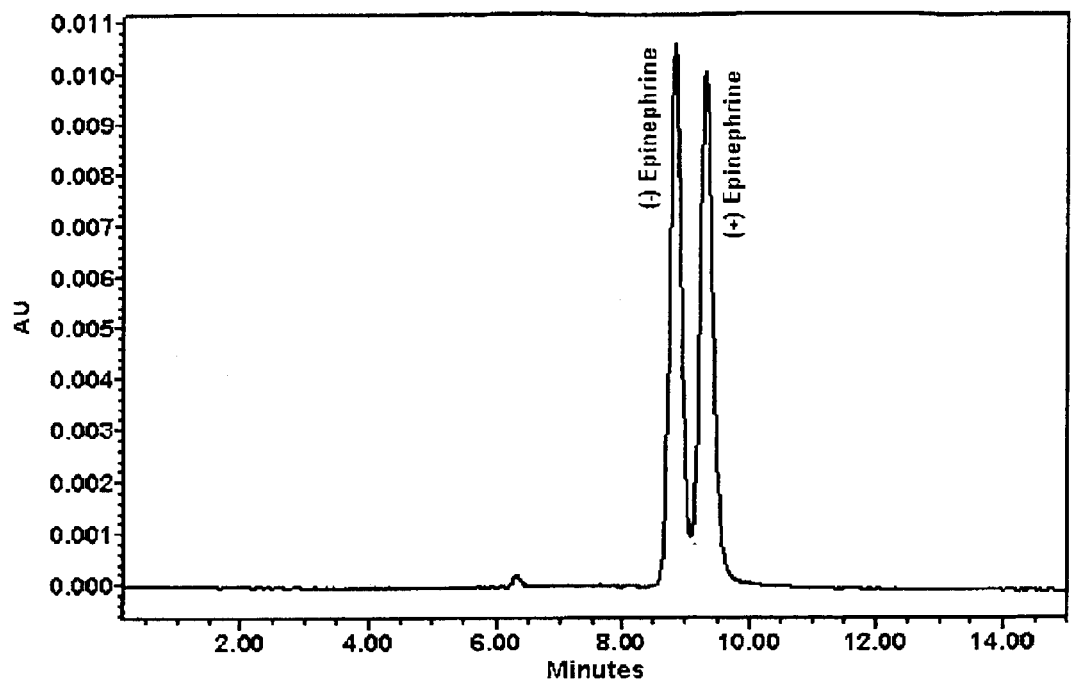
FIG. 1 is a HPLC chromatogram of racemic epinephrine monitored at 289 nm.

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Recently, trifluoromethylepinephrine compounds, (R)-2-trifluoromethylepinephrine (R) and (S)-2-trifluoromethylepinephrine (S), having the following structural formulas were synthesized:

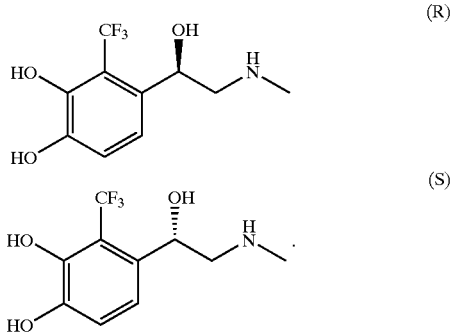

As used herein, a "trifluoromethylepinephrine compound" refers to an epinephrine derivative having a trifluoromethyl group attached to the benzene ring. As used herein, an "epinephrine derivative" refers to a compound having the following structural formula:

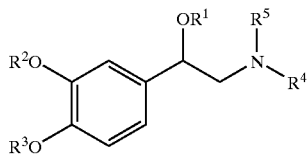

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, heteroarylthio, and the like.

Thus, a trifluoromethylepinephrine compound of the present invention includes compounds having the following structural formula (I):

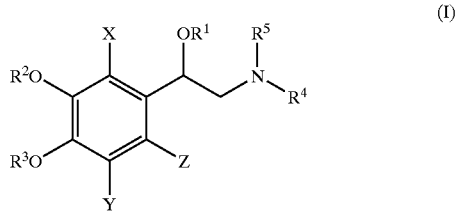

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, heteroarylthio, and the like, and wherein X, Y, and Z are each independently selected from the group consisting of H or trifluoromethyl with the proviso that at least one of which is trifluoromethyl. In preferred embodiments, $R^1$–$R^5$ are each independently selected from the group consisting of H and methyl and X is trifluoromethyl, more preferably, $R^1$–$R^3$, Y, and Z are H, $R^4$ is methyl, $R^5$ is H, and X is trifluoromethyl.

As described herein, the trifluoromethylepinephrine compounds of the present invention may exhibit a shelf storage stability that is longer than known epinephrine derivatives.

Catecholamines are biologically important compounds with functional groups susceptible to degradation upon storage. Epinephrine, a key ingredient in certain ophthalmic, bronchodilator and cardiac stimulant pharmaceuticals, functions as a catecholamine vasoconstrictor in amide based local-anesthetic formulations. See Yagiela (1998) Local Anesthetics. In: PHARMACOLOGY AND THERAPEUTICS FOR DENTISTRY. 4th ed. Yagiela J A, Neidle E A, Dowd F J, editors. St. Louis, Mo.: Mosby, pp. 217–234, which is herein incorporated by reference. The compound possesses a chiral carbon and is optically active, with the (R)-enantiomer (1a) exhibiting 15–20 times more biological activity than the (S)-enantiomer (1b). See Hondrum, S. O., et al. (1993) Anesthesia and Pain Control in Dentistry 2:198–202 and references therein. There are reports of epinephrine-containing local anesthetic failure not attributed to patient/provider factors but correlated to storage conditions. See Hondrum et al. (1993). Classically, most amides such as lidocaine require prolonged heating in the presence of strong acid or base to effect degradation. See Smith and March (2001). Aliphatic Nucleophilic Substitution. In: MARCH'S ADVANCED ORGANIC CHEMISTRY 5th ed. Smith M B, March J, editors. New York: Wiley & Sons, Inc., pp. 389–674, which is herein incorporated by reference. Epinephrine, however, is much more sensitive to relatively mild environmental conditions as above ambient temperatures and oxidation. Previous efforts to quantitate the enantiomeric excess of epinephrine involve either a biological in vivo assay or derivatization of the epinephrine followed by in vitro quantitative analysis. See Welsh (1955) J. Am. Pharm. Assoc. 44:507–514, which is herein incorporated by reference.

The chemical mechanism of vasoconstrictor loss in anesthetic samples via identification and quantitation of degradation products was ascertained according to Example 1. Five amide-based local anesthetic samples comprising epinephrine were studied. Individual carpules were exposed to above ambient temperatures (about 60° C.). Aliquots (10 µl) were analyzed at predetermined times. The solid phase selected was a Cyclobond I2000 RSP column (Advanced Separation Technologies, Inc., Whippany, N.J.) (250 mm×4.6 mm, 5 µm), the mobile phase was 100 mM phosphate buffer (pH=4) with a flow rate of 0.5 ml/min. The epinephrine enantiomers were detected at 280 nm. The results suggest that the biologically active form of epinephrine degrades via racemization and via addition of antioxidant.

Therefore, as described herein, the present invention provides trifluoromethylepinephrine compounds, compositions comprising trifluoromethylepinephrine compounds, methods of making trifluoromethylepinephrine compounds, and methods of using trifluoromethylepinephrine compounds for treating, preventing, or inhibiting pain, inducing vasoconstruction, or both in a subject.

The terms and abbreviations used in the instant disclosure have their normal meanings unless otherwise designated.

As used in the present application, the following definitions apply:

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both stereoisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

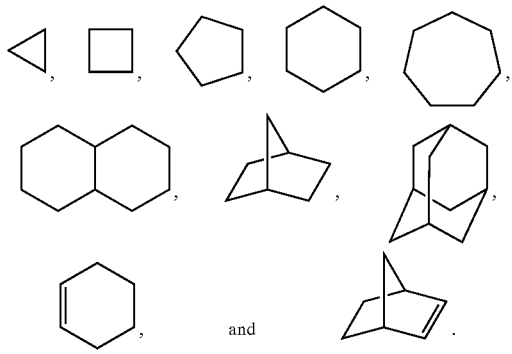

A "heterocycloalkyl group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

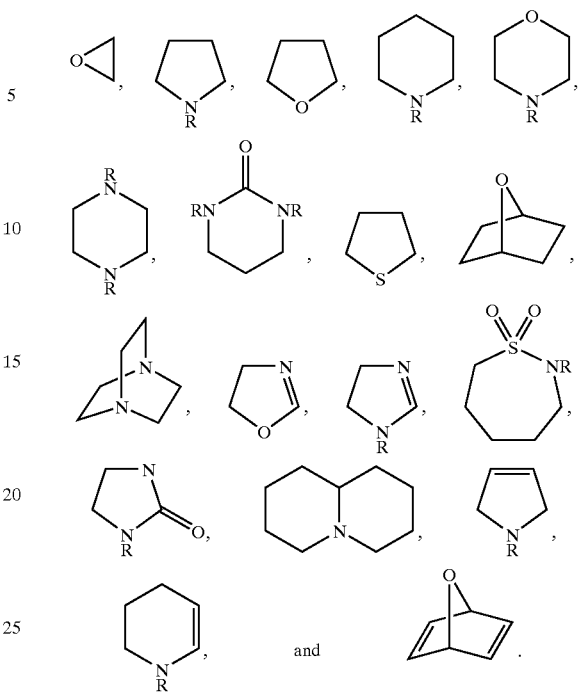

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bn). Illustrative examples of aryl groups include the following moieties:

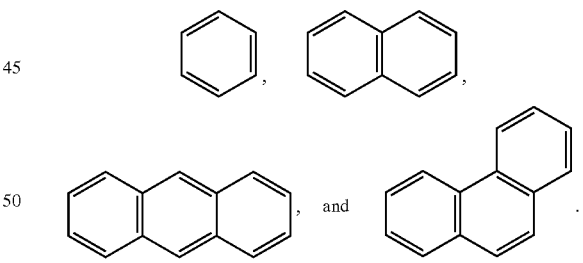

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

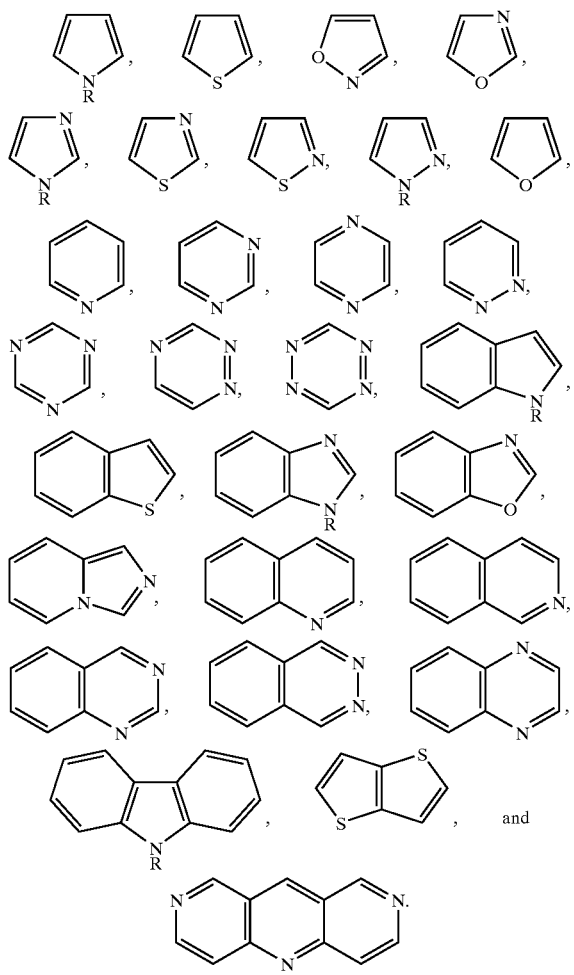

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R^a$ radical, where $R^a$ is a suitable substituent as defined below.

A "thioacyl group" is intended to mean a —C(S)—$R^a$ radical, where $R^a$ is a suitable substituent as defined below.

A "sulfonyl group" is intended to mean a —$SO_2R^a$ radical, where $R^a$ is a suitable substituent as defined below.

A "hydroxy group" is intended to mean the radical —OH.

An "amino group" is intended to mean the radical —$NH_2$.

An "alkylamino group" is intended to mean the radical —$NHR^a$, where $R^a$ is an alkyl group.

A "dialkylamino group" is intended to mean the radical —$NR^aR^b$, where $R^a$ and $R^b$ are each independently an alkyl group.

An "alkoxy group" is intended to mean the radical —$OR^a$, where $R^a$ is an alkyl group. Exemplary alkoxy groups include methoxy, ethoxy, propoxy, and the like.

An "alkoxycarbonyl group" is intended to mean the radical —C(O)$OR^a$, where $R^a$ is an alkyl group.

An "alkylsulfonyl group" is intended to mean the radical —$SO_2R^a$, where $R^a$ is an alkyl group.

An "alkylaminocarbonyl group" is intended to mean the radical —C(O)$NHR^a$, where $R^a$ is an alkyl group.

A "dialkylaminocarbonyl group" is intended to mean the radical —C(O)$NR^aR^b$, where $R^a$ and $R^b$ are each independently an alkyl group.

A "mercapto group" is intended to mean the radical —SH.

An "alkylthio group" is intended to mean the radical —$SR^a$, where $R^a$ is an alkyl group.

A "carboxy group" is intended to mean the radical —C(O)OH.

A "carbamoyl group" is intended to mean the radical —C(O)$NH_2$.

An "aryloxy group" is intended to mean the radical —$OR^c$, where $R^c$ is an aryl group.

A "heteroaryloxy group" is intended to mean the radical —$OR^d$, where $R^d$ is a heteroaryl group.

An "arylthio group" is intended to mean the radical —$SR^c$, where $R^c$ is an aryl group.

A "heteroarylthio group" is intended to mean the radical —$SR^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, PROTECTIVE GROUPS IN ORGANIC SYNTHESIS, $3^{rd}$ ed. John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether; O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while compounds of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the present invention also include active tautomeric and stereoisomeric forms, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

The compounds of the present invention may be prepared using reaction routes, synthesis schemes and techniques available in the art using starting materials that are readily available. The compounds of the present invention were made according to the following schemes and methods. However, it should be noted that the compounds of the present invention may be made other methods known in the art.

As shown in Scheme 1, the (R)- and (S) 2-trifluoromethylepinephrine compounds of the present invention may be prepared using 3,4-dihydroxy-2-trifluoromethyl-benzaldehyde (1) as a starting product.

Scheme 1:
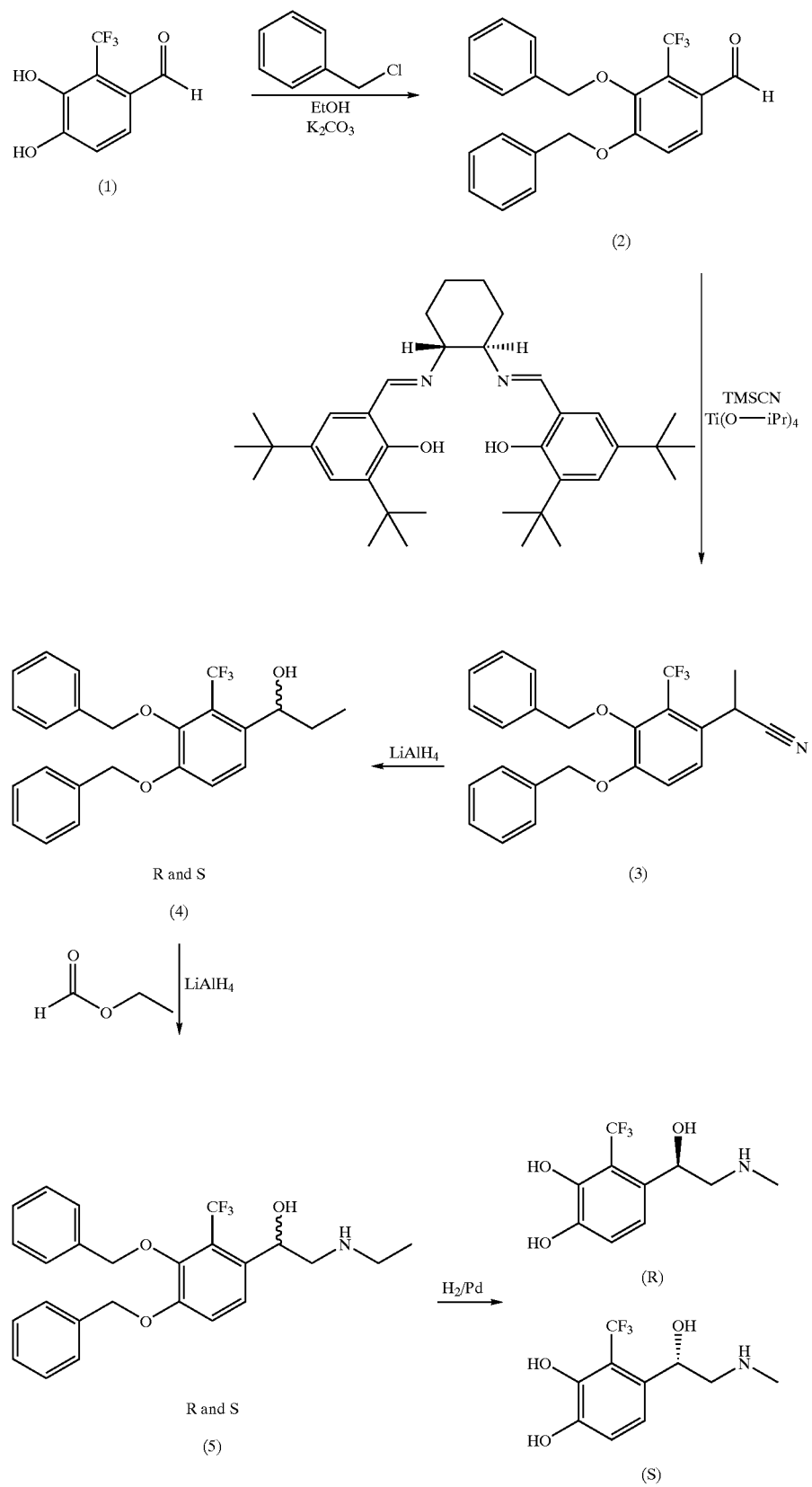

As used herein, the (R)- and (S)-2-trifluoromethylepinephrine compounds of the present invention were made according to the following Scheme 2:

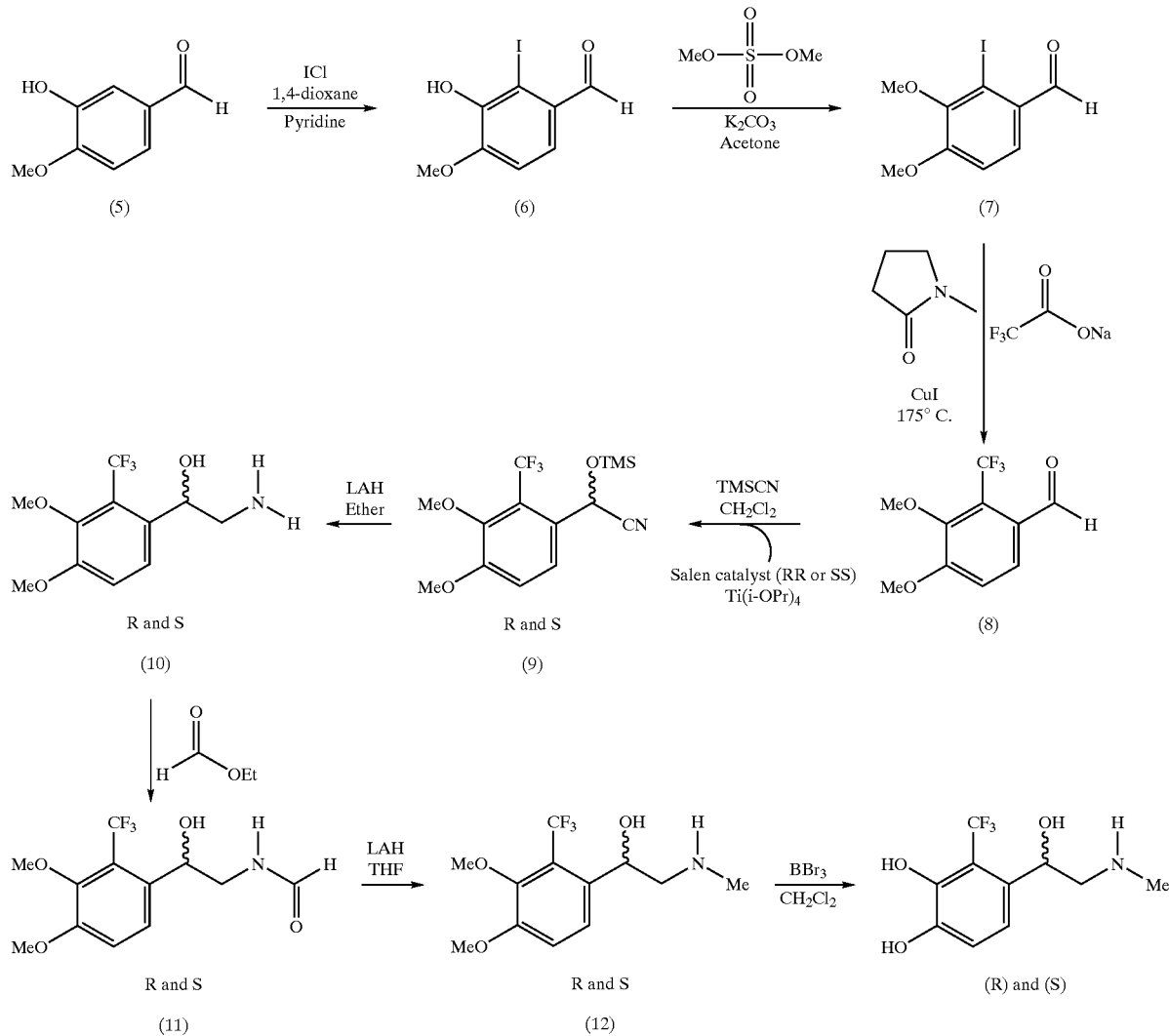

As shown above, 3-hydroxy-2-iodo-4-methoxybenzaldehyde (2-iodoisovanillin) (6) may be made by methods known in the art. See Miller et al. (1992) J. Med. Chem. 35:466–479, which is herein incorporated by reference. Specifically, a solution of ICl (27.22 g, 168.0 mmol) in dioxane (164 ml) was added dropwise to a stirred solution of 3-hydroxy-4-methoxybenzaldehyde (isovanillin) (5) (25.52 g, 167.9 mmol) in pyridine (96 ml) at 0° C. in a 1000 ml triple neck flask. The flask was plugged with a white rubber septum and an Ar balloon and needle were used. The mixture was stirred for about 6 days at room temperature.

The solvent was then removed in vacuo which yielded an oil. 400 ml of water was added and 6 N HCl was used to make the solution acidic by placing the flask in an ice bath and carefully adding the HCl solution dropwise, while periodically checking the pH with pH paper (pH ~2). A brown precipitate was formed which was filtered via a large Buchner funnel and washed 2 times with 200 ml water. The solid was added to 1200 ml $CH_2Cl_2$ in a 4 L Erlenmeyer flask. The mixture was magnetically stirred until the precipitate was dissolved. The solution was transferred to a separatory flask and extracted once with 700 ml of 5% potassium metabisulfite, once with 700 ml water, and twice with 350 ml saturated NaCl. The extract was dried over a small amount of $MgSO_4$, filtered, and then the solvent was removed in vacuo to give a yellow solid. The solid was recrystallized from ethyl acetate to yield yellow needles. mp 169–171° C.; MS m/z=278. $^1$H NMR (400 MHz) δ 10.04 (s, 1H), 7.55 (d, 1H, J=8.4 Hz), 6.93 (d, 1H, J=8.4 Hz), 6.34 (bs, 1H), 4.00 (s, 3H). $^{13}$C NMR in $CDCl_3$ (100.5 MHz) 194.7, 150.7, 145.7, 128.7, 123.8, 110.0, 88.0, 56.6.

2-iodo-3,4-dimethoxybenzaldahyde (7) was prepared according to methods known in the art. See Miller et al. (1992). Specifically, potassium carbonate (37.20 g, 269 mmol) and dimethyl sulfate (26.04 ml, 275 mmol, d=1.333, 34.71 g) was added to a stirred solution of 3-hydroxy-2-iodo-4-methoxybenzaldehyde (6) (37.32 g, 134 mmol) in acetone (372 ml, bp=56° C.). A 1000 ml triple neck flask equipped with a stir bar, reflux condenser and rubber septa was used. A gas-tight syringe was used to perform the addition. The solution was refluxed for 6 hours and then cooled to room temperature.

The solvent was then removed in vacuo. 160 ml water was added and the solution was extracted in a 500 ml separatory funnel twice with 160 ml diethyl ether. The diethyl ether extracts were combined and then washed with 160 ml water. The ether layer was separated and dried over small amount of $MgSO_4$, filtered, and the solvent was removed in vacuo to yield an oil that darkens upon standing. Purification was effected by vacuum distillation at an oil bath temperature of 170° C. at 0.165 torr followed by recrystallization from dichloromethane/pet ether to yield a white crystal: mp 75–78° C.; MS m/z=292. $^1$H NMR (400 MHz) δ 10.02 (s, 1H), 7.71 (d, 1H, J=8.4 Hz), 6.98 (d, 1H, J=9.2 Hz), 3.97 (s, 3H), 3.87 (s, 3H). $^{13}$C NMR in $CDCl_3$ (100.5 MHz) 195.0, 157.8, 148.9, 129.1, 127.5, 112.0, 100.3, 60.5, 56.3.

3,4-dimethoxy-2-(trifluoromethyl)benzaldehyde (8) was prepared according to methods known in the art. See Miller et al. (1992), Matsui et al. (1981) Chem. Lett. 1710–1720, which is herein incorporated by reference. Specifically, CUI (24.11 g, 126.6 mmol) and sodium trifluoroacetate (34.43 g, 253.2 mmol) was added to a solution of 2-iodo-3,4-dimethoxybenzaldehyde (7) (18.48 g, 63.31 mmol) in N-methyl-2-pyrrolidinone (360 ml, bp=81° C./10 mm) under anhydrous conditions. A 1000 ml single neck flask equipped with a stir bar and flowing Ar via an adapter was used. At 165° C. $CO_2$ was liberated. Then the solution was heated to 175° C. for 4 hours followed by cooling to room temperature.

The contents of the flask were added to 700 ml water with stirring. Then the mixture was stirred for 0.5 hour and then centrifuge at 25° C. at 3700 rpm for 15 minutes. The supernatant was decanted into a separatory funnel and extracted 3 times with 500 ml diethyl ether. The ether layers were combined and then washed with 500 ml brine. Flash chromatograph twice using $CH_2Cl_2$ (100%) followed by EtOAc/hexane (20/80) yielded 3,4-dimethoxy-2-(trifluoromethyl)benzaldehyde (8) as a yellow oil; MS m/z= 234. $^1$H NMR (400 MHz) δ 10.28 (s, 1H), 7.81 (d, 1H, J=9.2 Hz), 7.16 (d, 1H, J=8.8 Hz), 3.98 (s, 3H), 3.91 (s, 3H). $^{13}$C NMR in $CDCl_3$ (100.5 MHz) 189.0, 158.0, 148.0, 128.1, 126.0, 124.6 (q, J=30 Hz), 124.1 (q, J=275 Hz), 114.5, 61.8, 56.3. $^{19}$F (376.2 Mz) –51.9.

(1R or 1S)-3,4-dimethoxy-2-tifluoromethyl-1-((trimethylsilyl)oxy)phenylacetonitrile (9) may be prepared according to methods known in the art. See Kirk et al. (2000) J. Med. Chem. 43:1611–1619, and Jacobsen, E. N., et al. (1991) JACS 113:7063; alternatively see Kirk et al. (1979) J. Med. Chem. 22:1493–1497, which are herein incorporated by reference. Specifically, a 250 ml single neck round bottom flask equipped with a magnetic stir bar was charged with a solution of salen (R,R) catalyst ((–)-N,N'-Bis(3,5-di-tert-butylsalicylidene)-1,2-cyclohexanediamine, MW=546.84, 1.08 g, 1.97 mmol) in $CH_2Cl_2$ (40 ml) followed by the addition of titanium tetraisopropoxide (MW= 284.26, 312 μl, d=0.963, 300.4 mg, 1.06 mmol). The solution was kept under Ar and stirred at room temperature for 1.5 hours. The flask was equipped with an addition funnel, the reaction mixture was then cooled to –50° C. (using dry ice/acetone bath) under an atmosphere of Ar, the addition funnel was charged with a solution of 3,4-dimethoxy-2-(trifluoromethyl)benzaldehyde (8) (MW=234.17, 2.98 g, 12.7 mmol) and TMSCN (MW=99.21, 6.72 ml, d=0.744, 5.00 g, 50.4 mmol) in $CH_2Cl_2$ (40 ml). The aldehyde solution was slowly added to the catalyst solution (about 0.5 hour). Upon completion of addition, the addition funnel was replaced with a secured septum and the flask placed in an environmental chamber and stirred at –50° C. After 5 days at –50° C., samples from environmental chamber were removed and warmed to room temperature. The solvent was removed in vacuo, purified via flash column (75:25 hex:EtOAc). MS for the S isomer m/z=333. $^1$H NMR for S isomer (300 MHz) δ 7.63 (d, 1H, J=9.1 Hz), 7.13 (d, 1H, J=8.8 Hz), 5.80 (s, 1H), 3.91 (s, 3H), 3.88 (s, 3H), 0.23 (s, 9H). $^{13}$C NMR for S isomer (75 MHz) δ 154.3, 148.7, 126.9, 124.3, 124.1 (q, J=275 Hz), 121.7 (q, J=29.4 Hz), 119.0, 115.3, 61.7, 60.3, 56.1, –0.3. $^{19}$F (282.8 Mz) –53.9. MS for the R isomer m/z=333. $^1$H NMR for R isomer (300 MHz) δ 7.62 (d, 1H, J=8.8 Hz), 7.13 (d, 1H, J=8.8 Hz), 5.80 (s, 1H), 3.91 (s, 3H), 3.88 (s, 3H), 0.22 (s, 9H). $^{13}$C NMR for S isomer (75 MHz) δ 154.3, 148.7, 126.9, 124.3, 124.1 (q, J=275 Hz), 121.7 (q, J=30.0 Hz), 119.0, 115.3, 61.7, 60.3, 56.1, –0.3. $^{19}$F (282.8 Mz) –53.9.

(1S)-2-amino-1-(3,4-dimethoxy-2-trifluoromethylphenyl)ethanol (10) was formed via LAH reduction according to methods known in the art. See Kirk et al. (2000), and (1991) JACS 113:7063. Specifically, the S TMS cyanohydrin (9) (8.71 mmol, MW=333.38, 2.9036 g) was dissolved in ether (50 ml) and added dropwise to a suspension of $LiAlH_4$ (MW=37.95, 1.649 g, 43.5 mmol) in ether (50 ml, 0° C.) then stirred at room temperature 3 hours. The reaction mixture was cooled in an ice bath and then quenched by carefully adding 1.65 ml $H_2O$, 1.65 ml 15% NaOH, 4.95 ml $H_2O$. Then the mixture was stirred until the precipitate was colorless. The suspension was filtered and the filter cake was washed 3 times with hot EtOAc. The product in the filtrate was purified by recrystallization from EtOAc/hexanes to yield the (1S)-2-amino-1-(3,4-dimethoxy-2-trifluoromethylphenyl)ethanol compound (10). Data for the S isomer. $^1$H NMR (400 MHz) δ 7.48 (d, 1H, J=9.2 Hz), 7.06 (d, 1H, J=8.8 Hz), 5.00 (m, 1H), 3.85 (s, 3H), 3.83 (s, 3H), 2.95 (m 1H), 2.59 (m 1H), 2.4–2.2 (bs, 2H). $^{13}$C NMR for S isomer (100.5 MHz) δ 152.4, 148.0, 134.0, 124.2 (q, J=270 Hz), 122.6 121.5 (q, J=30.0 Hz), 115.3, 69.8, 61.4, 55.9, 49.4. $^{19}$F (282.8 Mz) –53.4.

(1R)-2-amino-1-(3,4-dimethoxy-2-trifluoromethylphenyl)ethanol (10) was formed via LAH reduction according to methods known in the art. See Kirk et al. (2000), and Jacobsen, E. N. et al. (1991) JACS 113:7063. Specifically, the R TMS cyanohydrin (9), 9.09 mmol, MW=333.38, 3.0300 g) was dissolved in ether (50 ml) and added to a suspension of $LiAlH_4$ (MW=37.95, 1.721 g, 45.3 mmol) in ether (50 ml, 0° C.) and stirred at room temperature for 3 hours. The reaction mixture was cooled in an ice bath and quenched by carefully adding 1.72 ml $H_2O$, 1.72 ml 15% NaOH, 5.16 ml $H_2O$. Then the mixture was stirred until the precipitate was colorless. The suspension was filtered and the filter cake was washed 3 times with hot EtOAc. The product in the filtrate was purified by recrystallization from EtOAc/hexanes to yield the (1R)-2-amino-1-(3,4-dimethoxy-2-trifluoromethylphenyl)ethanol compound (10). Data for the R isomer. $^1$H NMR (400 MHz) δ 7.48 (d, 1H, J=8.8 Hz), 7.06 (d, 1H, J=9.2 Hz), 5.01 (m, 1H), 3.85 (s, 3H), 3.83 (s, 3H), 2.98 (m 1H), 2.58 (m 1H), 2.5–1.9 (bs, 2H). $^{13}$C NMR for R isomer (100.5 MHz) δ 152.4, 148.1, 134.0, 124.5 (q, J=270 Hz), 122.6, 121.5 (q, J=30.0 Hz), 115.3, 69.8, 61.5, 55.9, 49.4. $^{19}$F (282.8 Mz) –53.3.

3.4-dimethoxy-2-(trifluoromethyl)-(N-methylamino) ethanol (12) was made according to methods known in the art. See Kirk et al. (2000). Specifically, a solution of (1S or 1R)-2-amino-1-(3,4-dimethoxy-2-trifluoromethylphenyl) ethanol (10) (MW=265.23, 3.00 g, 11.3 mmol) in ethyl formate (140 ml) was heated to reflux under an atmosphere of Ar for 3 hours with stirring. The suspension eventually goes into solution during the first hour of reflux. Upon completion, the reaction was allowed to cool to room temperature. Volatiles were removed in vacuo to afford 1-N-[2-(3,4-dimethoxy-2-trifluoromethylphenyl)-2-hydroxyethyl]formamide (11) as a low melting yellowish solid. To a cold (0° C.) suspension of LiAlH₄ (MW=37.95, 95%, 2.4 g, 63.2 mmol) in THF (30 ml) under Ar a solution of formamide (11) (MW=293.24, 13.0 mmol, 3.81 g) in THF (70 ml) was added dropwise. The mixture was heated to reflux for 3 hours and then cooled to 0° C. and quenched by the addition of 2.4 ml H₂O, 2.4 ml 15% NaOH and 7.2 ml H₂O. The mixture was stirred at room temperature until all of the unreacted LAH has reacted. The solid was filtered and washed 5 times with 50 ml of hot EtOAc. The filtrate was concentrated and the residue was recrystallized from hex/ EtOAc. For S isomer: mp=121–128° C. ¹H NMR for S in CDCl₃ (300 MHz) δ 7.53 (m, 1H, J=8.8), 7.06 (m, 1H, J=8.8), 5.16 (m, 1H), 3.86 (s, 3H), 3.82 (s, 3H), 2.80 (m, 1H), 2.56 (m, 1H), 2.42 (s, 3H). ¹³C NMR in CDCl₃ (75 MHz) 152.5, 148.1, 133.8, 124.5 (q, J=274 Hz), 122.8, 121.3, 115.5, 66.8, 61.5, 59.2, 55.9, 35.5. ¹⁹F (282.8 Mz) −53.4. For R isomer: mp=125–127° C. ¹H NMR for R in CDCl₃ (300 MHz) δ 7.55 (m, 1H, J=8.8), 7.06 (m, 1H, J=8.8), 5.22 (m, 1H), 3.86 (s, 3H), 3.84 (s, 3H), 2.83 (m, 1H), 2.62 (m, 1H), 2.47 (s, 3H). ¹³C NMR in CDCl₃ (75 MHz) 152.3, 148.1, 133.6, 124.5 (q, J=274 Hz), 122.9, 121.3, 115.5, 66.6, 61.6, 58.9, 56.0, 35.2. ¹⁹F (282.8 Mz) −53.4.

Both the S- and R-isomers of compound (12) were analyzed via HPLC using the Chirobiotic T column with a guard column. The column was washed with 5 column volumes of MeOH at 0.3 ml/min. The solvent was swapped over to MeOH/AcOH/Et3N 100:0.1:0.1 (prepared with 1 liter of MeOH and add 1 ml acetic acid and 1 ml triethylamine, vortexed, and filtered using a Teflon® membrane). The column was washed with 5 column volumes of MeOH/AcOH/Et3N at 0.3 ml/min. One mg of each isomer was dissolved in 4 ml MeOH. About 1 ml was placed in the HPLC autosample vials and labeled. Shoot 10 μl of each. The peak corresponding to the R isomer elutes at about 42.5 minutes. The peak corresponding to the S isomer elutes at about 44.6 minutes. Enantiomeric excess for both isomers is greater than about 97%.

2-trifluoromethylepinephrine (R) and (S) was prepared from 3,4-dimethoxy-2-(trifluoromethyl)-(N-methylamino) ethanol (12) by adding to a 25 ml round bottom flask containing a magnetic stir bar 0.2014 g of 3,4-dimethoxy-2-(trifluoromethyl)-(N-methylamino)ethanol (12) (0.7212 mmol) followed by 5 ml CH₂Cl₂. A rubber septum was inserted and a balloon containing argon was attached. The flask was cooled to −50° C. with stirring and a solution of BBr₃ (7 ml, 1.0M in CH₂Cl₂, 7.0 mmol) was added via syringe over a period of 10 minutes. Upon completion of addition the solution was warmed to room temperature and stirred for 24 hours. Then the flask was placed in ice bath and carefully quenched with 7 ml water. The precipitate was filtered off and the filtrate was transferred to a tared 50 ml round bottom flask. CH₂Cl₂ was removed in vacuo and water was removed via a lyophilizer to yield a brown solid. ¹H NMR for S isomer in D₂O (300 MHz) δ 7.04 (m, 2H), 5.26 (m, 1H), 3.13 (m, 1H), 2.68 (s, 3H). ¹³C NMR in D₂O (75 MHz) 145.5, 143.7, 130.3, 124.7 (q, J=275 Hz), 119.3, 118.6, 114.2, 64.9, 55.1, 33.1. ¹⁹F (282.8 Mz) −52.95. ¹H NMR for R isomer in D₂O (300 MHz) δ 7.12 (m, 2H), 5.33 (m, 1H), 3.20 (m, 1H), 2.72 (s, 3H). ¹³C NMR in D₂O (75 MHz) 148.1, 145.5, 130.3, 124.7, 122.9, 118.7, 112.3, 64.9, 55.0, 32.0. ¹⁹F (282.8 Mz) −52.95.

Therefore, the present invention also provides novel synthetic pathways and methods of making trifluoromethyl-ephinephrine compounds of the present invention.

Additional trifluoromethylepinephrine compounds of the present invention may be made according to the following:

5-trifluoromethylepinephrine (19) may be prepared by the following Scheme 3:

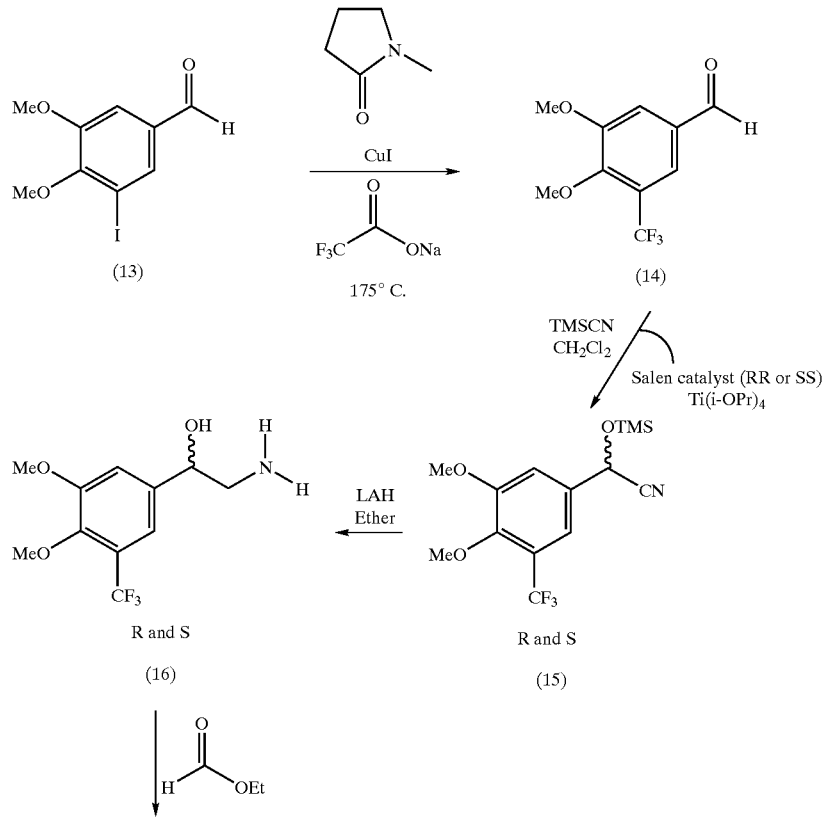

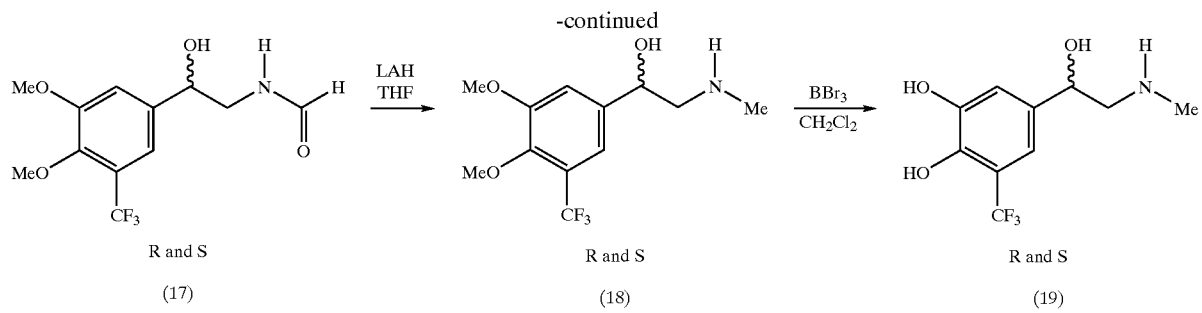

6-trifluoromethylepinephrine (28) may be prepared according to the following Scheme 4:

cursors and salts of such metabolites of the compounds having the structural formulas described herein.

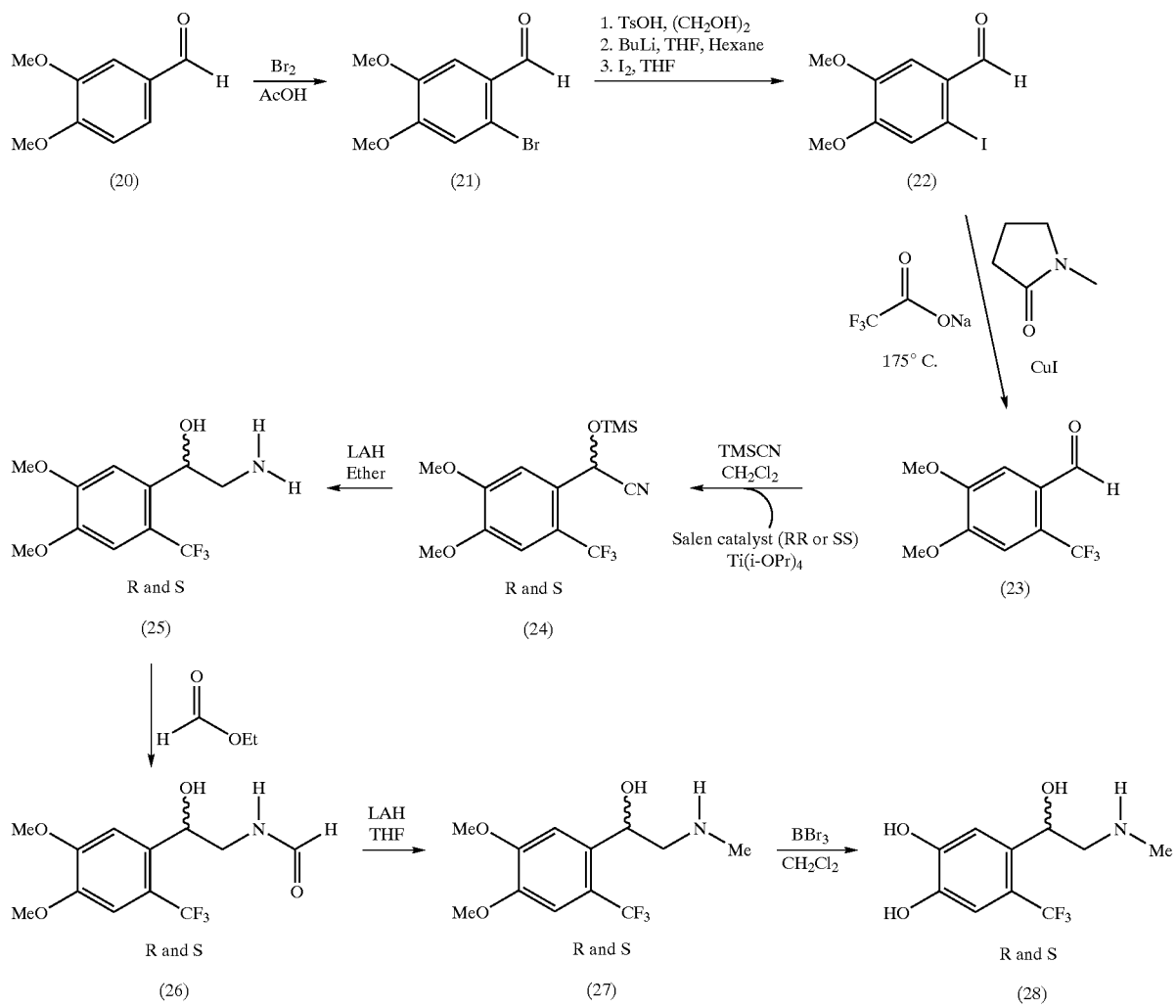

Therefore, the present invention also provides novel synthetic pathways and methods of making trifluoromethylephinephrine compounds of the present invention. The present invention also provides trifluoromethylephinephrine intermediates such as compounds (9), (10), (11), and (12) and methods of making thereof.

Additionally, the trifluoromethylepinephrine compounds of the present invention include pharmaceutically acceptable salts, multimeric forms, prodrugs, active metabolites, pre- The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (See, for example, Lee et al., (1984) Biochem. 23:4255, which is herein incorporated by reference). The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J. Pharm. Sci.*, 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs*, Drug Design and Development Krogsgaard-Larsen et al., eds., Harwood Academic Publishers, 1991, which are herein incorporated by reference.

If the trifluoromethylepinephrine compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the trifluoromethylepinephrine compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified structural formulas.

The anesthetic activity, vasoconstrictor activity, or both of the trifluoromethylepinephrine compounds may be measured by any of the methods available to those skilled in the art, including in vitro and in vivo assays. Examples of suitable assays for activity measurements are provided herein. Properties of the trifluoromethylepinephrine compounds may be assessed, for example, by using one or more of the assays set out in the Examples below. Other pharmacological methods may also be used to determine the efficacy of the compounds as anesthetics and vasoconstrictors.

The trifluoromethylepinephrine compounds in accordance with the present invention may be useful in the treatment of diseases or disorders associated with vasodialation in a subject. As used herein, diseases or disorder associated with vasodialation include bronchospasms, anaphylactic reactions, cardiac arrest, glaucoma, allergic reactions, and the like.

The trifluoromethylepinephrine compounds of the present invention may be used in combination with or as a substitution for treatments of the above conditions. For example, the trifluoromethylepinephrine compounds may also be used alone or in combination with a supplementary active compound such as lidocaine, etidocaine, mepivacaine, bupivacaine, prilocaine, articaine, procaine, propoxycaine, tetracaine, cocaine, benzocaine, dyclonine, and any other compound used as a local anesthetic.

A trifluoromethylepinephrine compound of the present invention may be administered in a therapeutically effective amount to a mammal such as a human. A therapeutically effective amount may be readily determined by standard methods known in the art. As used herein, a "therapeutically effective amount" of a trifluoromethylepinephrine compound of the present invention is an amount that will stimulate adrenergic receptors and achieve localized vasoconstriction in a subject as compared to a control. The therapeutically effective amount may be readily determined by conventional methods known in the art.

As defined herein, a therapeutically effective amount of a compound of the invention ranges from about 0.01 to about 100 mg/kg body weight, preferably about 0.1 to about 50 mg/kg body weight, and more preferably about 1 to about 10 mg/kg body weight. Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of a trifluoromethylepinephrine compound preferably includes a single treatment, but can include a series of treatments.

In a preferred example, a subject is treated with a compound of the invention in the range of between about 1 to about 5 mg/kg body weight, at least once. The subject may be treated with a compound of the invention in the range of between about 1 to about 5 mg/kg body weight from about one time per week to about once daily for about 5 to about 7 days or more. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given trifluoromethylepinephrine compound. Administration of prodrugs may be dosed at weight levels that are chemically equivalent to the weight levels of the fully active forms.

The trifluoromethylepinephrine compounds of the invention can be incorporated into pharmaceutical compositions suitable for administration. Pharmaceutical compositions of this invention comprise a therapeutically effective amount of a trifluoromethylepinephrine compound having the structural formulas (I), (R), (S), (19), or (28), and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl-methacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include lidocaine, etidocaine, mepivacaine, bupivacaine, prilocaine, articaine, procaine, propoxycaine, tetracaine, cocaine, benzocaine, dyclonine and any other compound used as a local anesthetic.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume. In an exemplary embodiment, the trifluoromethylepinephrine compound of the present invention is dissolved in DMSO and diluted with water.

The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the trifluoromethylepinephrine compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The in vitro assays of the prior art to determine the concentration of epinephrine enantiomers in pharmaceutical formulations poses a problem due to interferences from other components and epinephrine concentrations below the limit of detection as a result of sample dilution. One of the first in vitro methods involved in vacuo removal of solvent followed by measurement of the optical rotation of the residue. See Welsh (1955). A similar method relied on formation and optical rotation measurements of the enantiomeric O,O,N-triacetyl derivatives of epinephrine. See Welsh (1955). Although the latter method allowed handling of the hydrophobic derivative in relatively manageable organic solvents, the assay imprecisely relied on quantitative yields of the reaction. Both methods relied on the absence of other optically active ingredients in the injection.

More recently, non-optical rotation methods involving the formation of diastereomeric derivatives of epinephrine were developed. These methods involve the formation of the 2,3,4,6-tetra-O-acetyl-β-D-glucopyranosylisothiocyanate (GITC) derivatives followed by reversed phase HPLC analysis. As with the older methods involving formation of the triacetyl derivatives, these methods relied on quantitative yields of the reaction. In addition, these methods involved laborious manipulation of the samples such as precipitation of the antioxidant with hazardous lead tetraacetate, and quenching of the excess GITC agent with hydrazine hydrate, a highly toxic cancer suspect agent. See Alligire, J. F., et al. (1985) J. Chromatography 325:249–254, and Yang and Xu (1989) Chirality 1:92–93, which are herein incorporated by reference. Commercial samples of adrenaline (epinephrine) were analyzed and the enantiomers directly quantitated by capillary electrophoresis (CE). See Fanali and Boček (1990) Electrophoresis 11:757–760, and Peterson and Trowbridge (1992) J. of Chromatography 603:298–301, which are herein incorporated by reference. Although the samples analyzed contained similar excipients found in lidocaine-based local anesthetics (sodium chloride, sodium metabisulfite), they did not contain lidocaine. The use of CE for the quantitative assay of a single enantiomer of epinephrine in local anesthetic formulations was recently reported. See Britz-Mckibbin, P., et al. (1998) The Analyst 123:1461–1463, and Britz-Mckibbin, P. et al., (1999) J. Chromatography A 853:535–540, which are herein incorporated by reference. This method allowed the direct injection of the formulation without prior manipulation of the sample, however, there was no mention of enantioselective separation of the epinephrine isomers.

As described in Example 1, the present invention also provides a chiral HPLC assay. Specifically, Example 1 discloses a chiral HPLC method on a known sample of racemic epinephrine (10 μl, 10 ppm) in 0.01 N HCl monitored at 280 nm (FIG. 1). The enantioselectivity of selected chiral stationary phases, ionic strength of the mobile phase, pH and flow rates were investigated. Optimal enantioselectivity was achieved using ammonium dihydrogen phosphate buffer as mobile phase with a Cyclobond I 2000 RSP (Advanced Separation Technologies, Inc., Whippany, N.J.) stationary phase. The retention times were 8.9 min and 9.4 min for 1a and 1b, respectively.

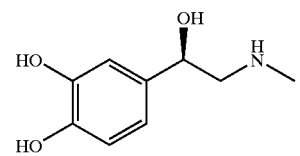

1a

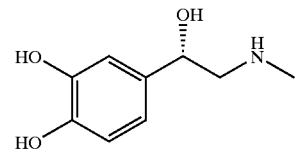

Figure 3:
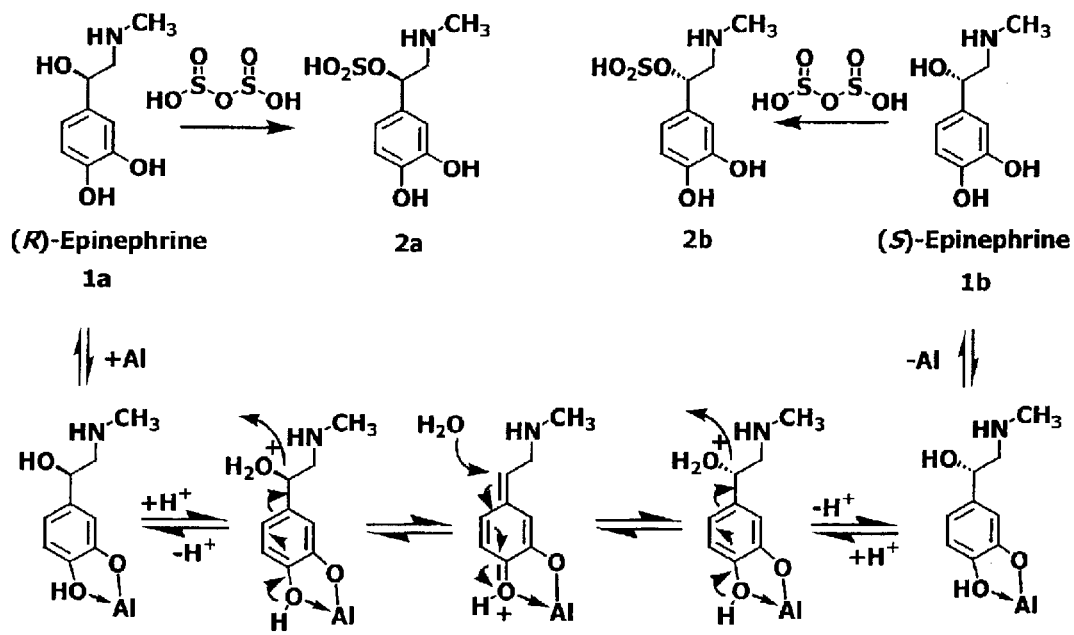
FIG. 3 is a mechanistic scheme for the degradation of (R)-epinephrine in amide-based local anesthetic injections.

1b elution order of the enantiomers was identified by comparison to the retention time of an authentic sample of 1a. The results show that of the five commercial brands investigated, samples of Octocaine® 100 and Henry-Schein® began to exhibit racemization in a relatively short period of time (1.2 days at 60° C.). One possible explanation of why the epinephrine in these samples substantially racemized at elevated temperatures is due to the absence of metal sequestering agents in the injections. Samples that display little or no racemization as Lignospan® Standard, 2% Xylocaine® and Cook-Waite™, contain either EDTA (e.g. Lignospan® Standard) or citric acid (e.g. 2% Xylocaine®, Cook-Waite™). Both EDTA and citric acid are known to form complexes with metal ions. See Budavari, S. THE MERCK INDEX. 11th ed. (1989). Rahway, N.J.: Merck & Co., Inc. p. 363, 550, which is herein incorporated by reference. Elemental analysis revealed the presence of trace amounts of aluminum in all samples. Solutions containing aluminum at concentrations as low as 2 ppm were reported to catalyze the degradation of epinephrine in the presence of bisulfite anion at 50° C. See Milano, E. A., et al. (1982) J. Parenter. Sci. Technol. 36:232–236, and Milano and Williams (1983) J. Parenter. Sci. Technol. 37:165–169, which are herein incorporated by reference. Mechanistically, aluminum may reversibly chelate 1a at the vicinal hydroxyl groups of the phenyl ring. See FIG. 3. An acid hydrolysis resulting in the elimination of water (all injections are labeled as buffered with a pH in the range of 3 to 5.5) renders an aluminum stabilized cation. Loss of stereochemical information, i.e., racemization, occurs when this species is attacked by water indiscriminately on either side of the chelated complex resulting in formation of both 1a and 1b.

All samples at 60° C. exhibited disappearance of total epinephrine indicative of a non-racemization degradation pathway. All HPLC chromatograms at 60° C. showed growth of a peak eluting at approximately 6.8 min (UV absorptions at $\lambda_{max}$=226 nm and $\lambda_{max}$=280 nm) with concomitant decrease of 1a. This peak was assigned as epinephrine sulfonic acid 2a (and enantiomer 2b), formed independently in our laboratory by the addition of potassium metabisulfite to 1a. See Schroeter and Higuchi (1960) J. Pharm. Sci. 49:331, which is herein incorporated by reference. Our attempts to resolve 2a and 2b using various chiral stationary phases were unsuccessful. The presence of 2a (and 2b) in the exposed carpules may be the result of a nucleophilic addition of the bisulfite antioxidant to epinephrine. This non-catalytic pathway is competing with racemization of 1a to 1b and may explain the decrease in the concentration of total epinephrine. See FIG. 3.

Therefore, the present invention provides a chiral HPLC method to determine both the biologically active and inactive forms of epinephrine in a sample. This method precludes chemical alteration of the sample such as derivatizing the epinephrine and it eliminates the need for removal of any component prior to analysis.

The following examples are intended to illustrate but not to limit the invention.

EXAMPLE 1

Quantitative Analysis Via Chiral HPLC Separation and UV-Vis Detection

HPLC analysis was performed using a Waters 600E 4-solvent delivery system or two Waters 515 pumps integrated with a pump control module (Waters, Milford, Mass.). Chiral separation of epinephrine was obtained using a Cyclobond I2000 RSP stationary phase (Advanced Separation Technologies, Inc., Whippany, N.J., 250 mm×4.6 mm, 5 μm particle size). The mobile phase was 100 mM ammonium dihydrogen phosphate buffer (adjusted to pH=4 using 100 mM phosphoric acid) at a flow rate of 0.5 ml/min. The stationary phase was periodically regenerated by sequentially passing several columns of ethanol, water and acetonitrile to minimize line broadening of the analytes. Both forms of epinephrine were monitored at 280 nm using a Waters 996 photodiode array detector (Waters, Milford, Mass.). Data handling and storage was accomplished using Millennium 32 (versions 3.05 and 3.20) Chromatograph Manager software (Waters, Milford, Mass.). Samples (10 μl) were injected using a Waters 717 plus autosampler (Waters, Milford, Mass.) with a 200 μl sample loop installed. (±)-Epinephrine hydrochloride, (−)-epinephrine (1a),

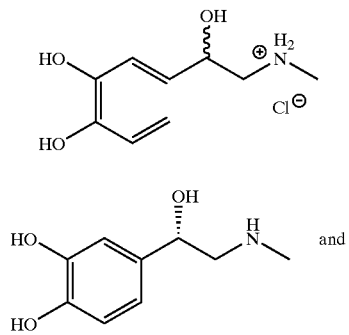
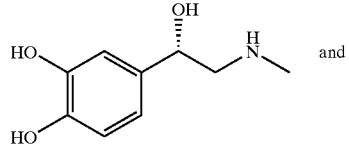

ammonium dihydrogen phosphate were purchased from Sigma-Aldrich (St. Louis, Mo.) and used as purchased. Elemental analysis was determined by ICPMS and performed by West Coast Analytical Services (Santa Fe Springs, Calif.).

Five commercially available 2% lidocaine-based local anesthetic injections were selected for analysis. The samples were Lignospan® Standard (Spécialités Septodont®, New Castle, Del.), Octocaine® 100 (Novocol, Cambridge, Ontario, Canada), 2% Xylocaine® (Astra®, Westborough, Mass.), Lidocaine HCl 2% (trademark Cook-Waite, distributed by Eastman Kodak Company, manufactured by Abbott Laboratories, North Chicago, Ill.) and Lidocaine HCl 2% (distributed by Henry-Schein®, manufactured by Novocol, Cambridge, Ontario, Canada). Each carpule was labeled with a total epinephrine concentration of 1:100,000 epinephrine:solution. All sample analyses were completed prior to the labeled expiration date. Individual carpules of each brand of local anesthetic were subjected to a temperature of 60° C. One carpule of each brand was selected to be a control (protected from light, kept at room temperature). Aliquots (about 25 μl) were withdrawn from each carpule at t=0, subsequent aliquots were analyzed from the same carpule at approximately every 24 hours for the first three days (about 4 day intervals thereafter).

Analysis of the epinephrine derivatives was obtained using a Cyclobond I 2000 RSP stationary phase (Advanced Separation Technologies, Inc., Whippany, N.J., 250 mm×4.6 mm, 5 μm particle size). The mobile phase was 100 mM ammonium dihydrogen phosphate buffer (adjusted to pH=4 using 100 mM phosphoric acid) at a flow rate of 0.5 ml/min. The stationary phase was periodically regenerated by sequentially passing several columns of ethanol, water and acetonitrile to minimize line broadening of the analytes. All derivatives of epinephrine possessing an aromatic moiety may be monitored at 280 nm using a Waters 996 photodiode array detector (Waters, Milford, Mass.). Data handling and storage was accomplished using Millennium 32 (versions 3.05 and 3.20) Chromatograph Manager software (Waters, Milford, Mass.). Crude samples were dissolved in an aqueous solution of 0.01 M HCl and injected using a Waters 717 plus autosampler (Waters, Milford, Mass.) with a 200 μl sample loop installed. Samples were typically analyzed at a running time of 40 minutes to allow for the complete elution of the lidocaine. 1a and 1b were monitored at 280 nm using photodiode array detection and identified by comparison of absorbance spectra and retention times from authentic samples of racemic epinephrine (See FIG. 1) and optically pure 1a. Quantitation of the enantiomers was obtained against a standard calibration curve of 1a.

Figure 2A:
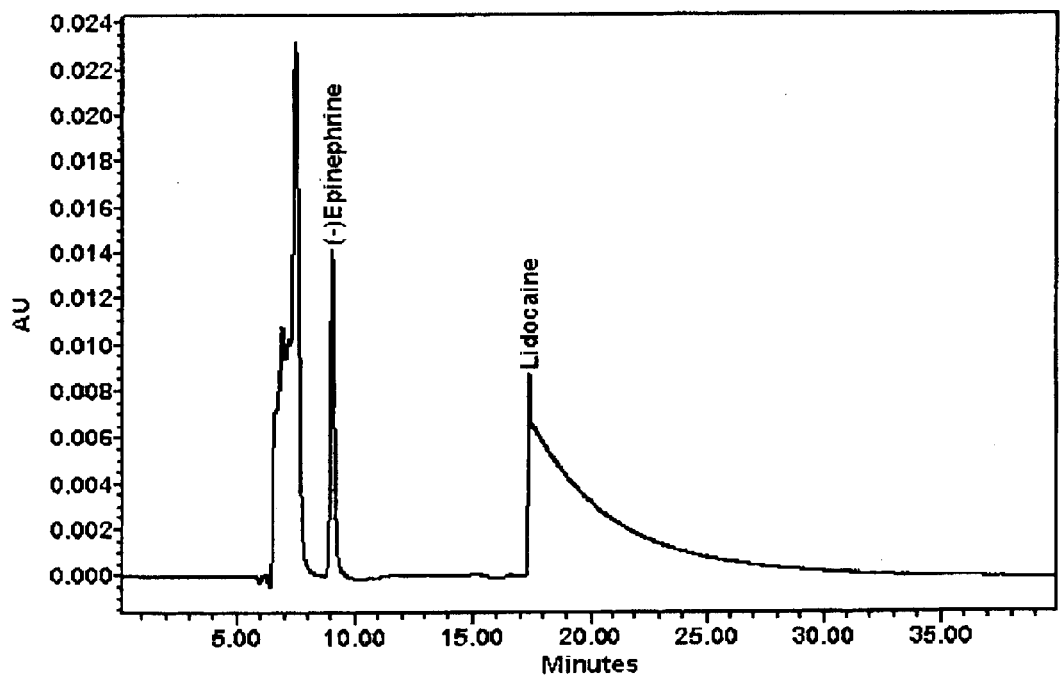
FIG. 2A is a HPLC chromatogram of Lignospan® Standard prior to thermal exposure, monitored at 280 nm.
Figure 2B:
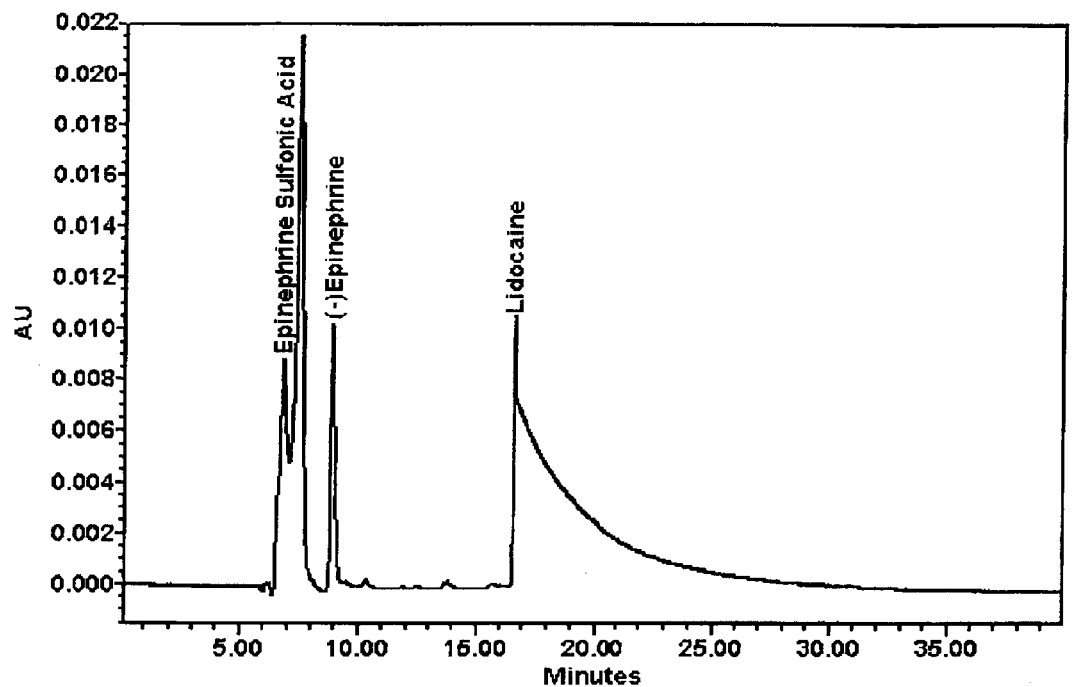
FIG. 2B is a PLC chromatogram of Lignospan® Standard aliquot, 20.7 days at 60° C., monitored at 280 nm.
Figure 2C:
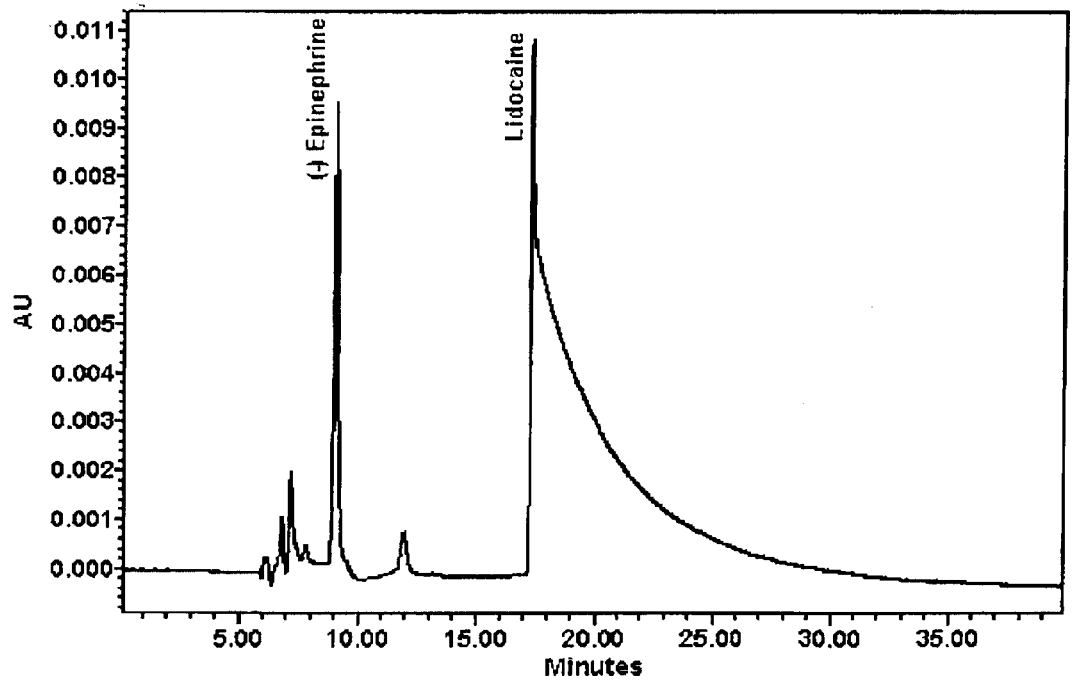
FIG. 2C is a HPLC chromatogram of Henry-Schein® prior to thermal exposure, monitored at 280 nm.
Figure 2D:
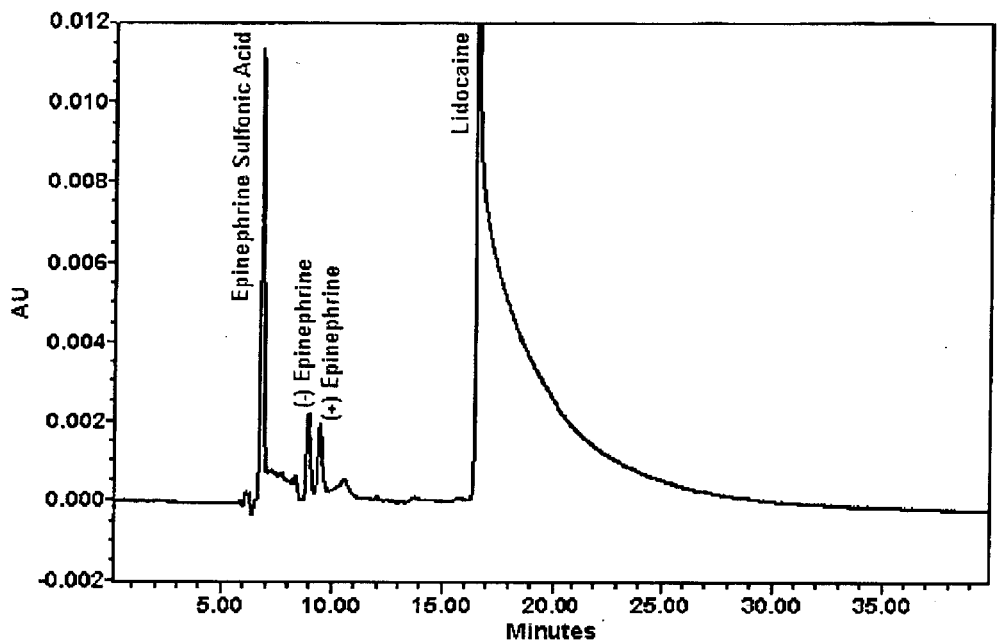
FIG. 2D is a HPLC chromatogram of Henry-Schein® aliquot, 20.7 days @ 60° C., monitored at 280 nm.

FIGS. 2A and 2C depict chromatograms of Lignospan® Standard (10 μl) and Henry-Schein® (10 μl) samples, respectively, prior to exposure to above ambient temperatures. At an above ambient temperature (60° C.) the Lignospan® Standard sample showed no 1b increase (FIG. 2B), however, at 60° C., 1b in the Henry-Schein® sample increased at the expense of 1a (FIG. 2D). Analysis of the concentrations of 1a, 1b and total epinephrine versus time at 60° C. revealed that 1a is racemizing in Octocaine® 100 and Henry-Schein® samples. See Table 1.

TABLE 1

Summary of HPLC Data* of 1a, 1b and Total Epinephrine Concentration at 60° C. Versus Time

| Time | Lignospan | | | Cook-Waite | | | Octocaine | | | Xylocaine | | | Henry-Schein | | |
|---|---|---|---|---|---|---|---|---|---|---|---|---|---|---|---|
| (days) | 1a | 1b | Total | 1a | 1b | Total | 1a | 1b | Total | 1a | 1b | Total | 1a | 1b | Total |
| 0.0 | 10.68 | 0.00 | 10.68 | 10.87 | 0.00 | 10.87 | 10.92 | 0.00 | 10.92 | 11.35 | 0.00 | 11.35 | 6.79 | 0.00 | 6.79 |
| 1.2 | 10.42 | 0.00 | 10.42 | 10.82 | 0.00 | 10.82 | 9.75 | 0.11 | 9.86 | **11.38 | 0.00 | 11.38 | **7.06 | 0.71 | 7.77 |
| 2.0 | 9.96 | 0.00 | 9.96 | 10.32 | 0.00 | 10.32 | 8.93 | 0.16 | 9.09 | 10.84 | 0.00 | 10.84 | 5.11 | 1.14 | 6.24 |
| 2.8 | 9.62 | 0.00 | 9.62 | 9.99 | 0.00 | 9.99 | 8.09 | 0.20 | 8.30 | 10.31 | 0.00 | 10.31 | 3.93 | 1.29 | 5.22 |
| 5.2 | 9.27 | 0.00 | 9.27 | 9.71 | 0.00 | 9.71 | 6.80 | 0.71 | 7.51 | 10.29 | 0.00 | 10.29 | 2.22 | 1.43 | 3.65 |
| 8.0 | 8.22 | 0.06 | 8.28 | 8.47 | 0.08 | 8.55 | 5.24 | 1.21 | 6.45 | 9.15 | 0.00 | 9.15 | 1.61 | 1.51 | 3.12 |
| 12.8 | 8.22 | 0.22 | 8.43 | 7.92 | 0.33 | 8.25 | 4.44 | 1.83 | 6.27 | 9.00 | 0.11 | 9.11 | 1.22 | 1.17 | 2.39 |
| 16.4 | 6.98 | 0.15 | 7.13 | 6.74 | 0.42 | 7.17 | 3.02 | 1.59 | 4.61 | 7.77 | 0.09 | 7.86 | 0.84 | 0.84 | 1.69 |
| 18.8 | 6.30 | 0.14 | 6.44 | 6.08 | 0.48 | 6.56 | 2.09 | 1.23 | 3.32 | 7.01 | 0.11 | 7.12 | 0.56 | 0.58 | 1.14 |
| 20.7 | 6.09 | 0.19 | 6.28 | 5.83 | 0.69 | 6.52 | 1.63 | 1.12 | 2.75 | 6.87 | 0.21 | 7.07 | 0.38 | 0.52 | 0.90 |

*Concentration data are reported in micrograms per milliliter
**Value is anomalously high due to slight peak broadening Samples of Lignospan® Standard, 2% Xylocaine® and Cook-Waite™ did not show appreciable racemization at 60° C.

All chromatograms of thermally exposed samples exhibited growth of a peak (at the expense of 1a) that eluted at 6.8 minutes with UV absorptions at $\lambda_{max}$=226 nm and $\lambda_{max}$=280 nm. This peak was assigned to unresolved enantiomers of epinephrine sulfonic acid (2a and 2b).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A compound having the following structural formula (I):

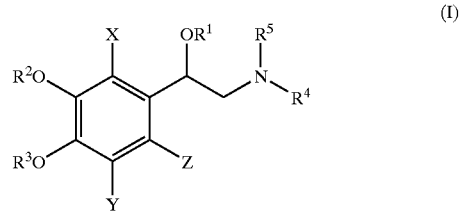

wherein $R^1$–$R^5$ are each independently selected from the group consisting of H, alkyl, alkoxyl, aryl, heteroaryl, cycloalkyl, heterocycloalkyl, acyl, thioacyl, sulfonyl mercapto, alkylthio, carboxy, amino, alkylamino dialkylamino, carbamoyl, arylthio, and heteroarylthio;

wherein X, Y, and Z are each independently selected from the group consisting of H or trifluoromethyl with the proviso that at least one of which is trifluoromethyl.

2. The compound of claim 1, wherein $R^1$–$R^5$ are each independently selected from the group consisting of H and methyl.

3. The compound of claim 1, wherein and X is trifluoromethyl.

4. The compound of claim 1, wherein and Y is trifluoromethyl.

5. The compound of claim 1, wherein and Z is trifluoromethyl.

6. The compound of claim 1, wherein $R^1$–$R^4$ are methyl.

7. The compound of claim 1, wherein $R^5$ is H.

8. The compound of claim 1, wherein the compound is 2-trifluoromethylepinephrine, 5-trifluoromethylepinephrine, or 6-trifluoromethylepinephrine.

9. The compound of claim 1, wherein the compound is an (S)-enantiomer.

10. The compound of claim 1, wherein the compound is an (R)-enantiomer.

11. A pharmaceutical composition comprising the compound of claim 1 and a pharmaceutically acceptable carrier.

12. The pharmaceutical composition of claim 11 and further comprising a supplementary active compound.

13. The pharmaceutical composition of claim 12, wherein the supplementary active compound is an analgesic.

14. The pharmaceutical composition of claim 13, wherein the analgesic is a local analgesic.

15. A compound having the following structural formula (9)

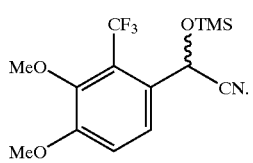

16. A compound having the following structural formula (10)

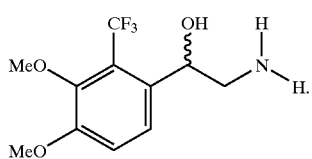

17. A compound having the following structural formula (11)

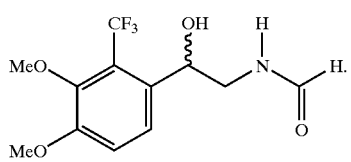

18. A compound having the following structural formula (12)

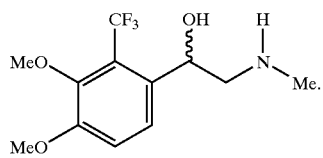

19. A method of making 2-trifluoromethylepinephrine which comprises using 3,4-dihydroxy-2-trifluoromethyl-benzaldehyde or 3-hydroxy-4-methoxybenzaldehyde as a starting product.

20. A method of inducing localized vasoconstriction in a subject which comprises administering to the subject the compound of claim 1.

21. The method of claim 20, wherein the compound is 2-trifluoromethylepinephrine, 5-trifluoromethylepinephrine, or 6-trifluoromethylepinephrine.

22. A method of treating a disease or a disorder associated with vasodialation in a subject which comprises administering to the subject the compound of claim 1.

* * * * *